United States Patent [19]

Bison et al.

[11] Patent Number: 4,652,671

[45] Date of Patent: Mar. 24, 1987

[54] PROCESS FOR THE PREPARATION OF DICHLOROISONITRILOCARBOXYLIC ACID ESTERS

[75] Inventors: Günter Bison, Troisdorf; Norbert Linkat, St. Augustin; Klaus Thewalt, Witten, all of Fed. Rep. of Germany

[73] Assignee: Dynamit Nobel Aktiengesellschaft, Troisdorf, Fed. Rep. of Germany

[21] Appl. No.: 775,354

[22] Filed: Sep. 12, 1985

Related U.S. Application Data

[60] Division of Ser. No. 619,919, Jun. 12, 1984, abandoned, which is a continuation of Ser. No. 475,726, Mar. 16, 1983, abandoned.

[30] Foreign Application Priority Data

Mar. 20, 1982 [DE] Fed. Rep. of Germany ....... 3210296
Mar. 20, 1982 [DE] Fed. Rep. of Germany ....... 3210297

[51] Int. Cl.$^4$ ............................................. C07C 119/18
[52] U.S. Cl. ..................................... 560/168; 548/253
[58] Field of Search ...................... 560/168; 260/543.2

[56] References Cited

PUBLICATIONS

Kuhle, Agnew. Chem. Internat. Edit., 6, pp. 649–665, (1967).

Primary Examiner—Michael L. Shippen
Attorney, Agent, or Firm—Antonelli, Terry & Wands

[57] ABSTRACT

It is suggested to produce 5-chloro-1H-tetrazolecarboxylic acid esters by reaction of dichloroisonitriloacetic acid esters with alkali or metal azides or ammonium azide.

The dichloroisonitriloacetic acid esters required for this purpose are formed by reacting N-formylaminocarboxylic acid esters with chlorine or with compounds which split off chlorine.

4 Claims, No Drawings

PROCESS FOR THE PREPARATION OF DICHLOROISONITRILOCARBOXYLIC ACID ESTERS

This is a division of application Ser. No. 619,919, filed June 12, 1984, now abandoned, which is a continuation of application Ser. No. 475,726, filed Mar. 16, 1983, now abandoned.

This invention relates to a process for the production of 5-chloro-1H-tetrazole-1-carboxylic acid esters. Processes for the preparation of the aforementioned compound are known (Can. J. Chem. 1969, 47 (5): 713–719; U.S. Pat. No. 3,468,874). These processes utilize as the starting material tetrazoles substituted in the 5-position by alkyl, alkoxy, amine, halogen, mercapto, etc., which are not readily accessible and are dangerous to prepare. The subsequent reaction of halocarboxylic acid esters leads to a mixture of isomers wherein the carboxylic acid ester group occurs at various positions on the ring.

Therefore, the present invention has the object of providing a process making it possible to prepare 5-chloro-1H-tetrazole-1-carboxylic acid esters in high purity and in a technically simple and nonhazardous fashion.

This invention is directed to a process for the preparation of 5-chloro-1H-tetrazole-1-carboxylic acid esters of the general formula:

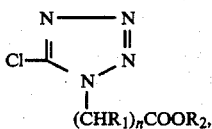

(CHR$_1$)$_n$COOR$_2$,   I wherein
R$_1$ is an alkyl group containing 1 to 2 carbon atoms or hydrogen, n is an integer of 1 to 4, and R$_2$ is an alkyl group containing 1 to 6 carbon atoms, characterized by reacting the correspondingly substituted dichloroisonitrilocarboxylic acid ester of the formula:

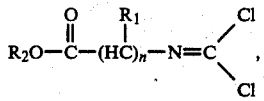

R$_2$O—C(=O)—(HC)$_n$—N=C(Cl)$_2$,   II wherein R$_1$, n, and R$_2$ have the meanings given above, with a alkaline azide of the formula:

MeN$_3$ wherein Me represents potassium, sodium, or ammonium; and isolating the reaction product.

The substituted dichloroisonitrilocarboxylic acid esters are derivatives of aliphatic aminocarboxylic acid esters; i.e., of the aminoacetic acid ester and its homologs.

The group —(CHR$_1$)$_n$— present in the product (I) and in the starting compound (II) can carry on one or several of the carbon atoms the substituent R$_1$; i.e., —CH$_3$ or —C$_2$H$_5$, of which —CH$_3$ is preferred. Preferably, when n is 1, the R$_1$ is hydrogen and the group —(CHR$_1$)$_n$— is then —CH$_2$— or when n is 2, the group —(CHR$_1$)$_n$— then is H$_3$C—CH$_2$— or —CH$_2$—CH$_2$—; and for certain cases, when n is 3, the group —(CHR$_1$)$_n$ is preferably —CH$_2$—CH$_2$—CH$_2$—.

The reaction can be conducted at temperatures of 10°–100° C., preferably 30°–90° C., very preferably at the boiling temperature of the reaction mixture in the range from 50° to 90° C. This reaction is often conducted in a batch-type reactor under autogeneous pressure with a reflux condenser. Generally the pressure may be between atmospheric pressure and 10 bar, though autogenous pressure is preferred.

Preferably, equimolar amounts of the dichloro compound of Formula II and of the alkaline azide are utilized; preferably the alkali metal azides are employed and more particularly, sodium azide.

The dichloroisonitrilocarboxylic acid ester of Formula II can be obtained according to known methods, especially from N-formylaminocarboxylic acid esters of the formula:

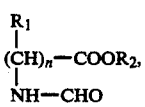

R$_1$
|
(CH)$_n$—COOR$_2$,   III
|
NH—CHO wherein R$_1$, n, and R$_2$ have the same meanings heretofore mentioned by reaction with chlorine or compounds splitting off chlorine in thionyl chloride.

The reaction of the starting compounds of Formula II with an alkali metal azide in water or an aqueous diluent, such as, for example, water/dimethoxyethane, water/acetone, or water leads in almost quantitative yield to the products of Formula I.

The preparation of tetrazoles with aryl substituents in the 5-position is described in J. Org. Chem. 32: 3580/92 (1967) using as starting compounds the stable aryl isocyanide dichlorides and reacting same with sodium azide. It was surprising that, according to this invention, the much more labile dichloroisonitrilocarboxylic acid esters of Formula II are amenable to this reaction and produce considerably better, namely, almost quantitative, yields. Surprisingly, there is neither a hydrolysis of the chlorine atom in the 5-position or of the carboxylic ester group in the 1-position, nor substitution thereof by an azido group.

The preparation of the products of Formula I is effected preferrably in a mixture of 5 to 80 wt.% water and 0.5 to 20 wt.% of a solvent miscible with water. The minimal amount of water used is that, which keeps the formed alkali or ammonium chloride in solution. Generally speaking, per weight unit of the reactant 1 to 10, preferably 2 to 5 weight units of said mixture of water and solvents are used.

The products prepared according to the process, specifically are utilized by converting into 5-Mercapto-1H-tetrazole-1-carboxylic acid by reaction of the products of Formula I with thiourea under acid condition to form the SH-group in 5-position and to form the acetic acid by hydrolysis of the ester in 1-position as more closely is described in example 9. This product of example 9 is used in generally known manner to form one of the side chains of antibiotics, for example of CEFORANIDE by forming the group

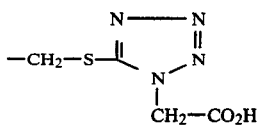

by splitting off acetic acid from the group —CH$_2$—O—COCH$_3$ of cephalosporanic acid. CEFORANIDE is a best known drug as may be seen from Annual Drug Data Report 1979/80 page 46.

The compounds of Formula II are reacted preferably in inert solvents or diluents, suitably by being added dropwise into water or a mixture of water and an inert organic solvent or diluent containing the alkaline azide in the dissolved form. Suitable organic solvents or diluents are ethers, such as dimethoxyethane and ketones, such as acetone.

The monoazides or diazides formed at low temperatures and being highly subject to decomposition are not produced according to our method.

After the reaction, the product is crystallized from the reaction mixture, for example, after removal of the organic diluent by distillation and cooling of the residual aqueous phase to 10° C. Without further purification, 5-chloro-1H-tetrazole-1-carboxylic acid esters are obtained in excellently pure form and in high yields.

The products prepared according to the process can be utilized, after exchange of the chlorine atom in the 5-position against other substituents, as side chains for the construction of penicillins and cephalosporins and, thus, are valuable intermediates. The chlorine atom can be replaced according to known methods, for example, by other substituents, such as hydroxy, nitrile, amine, alkoxy, or mercapto, as well as their alkylation products (—S—CH$_2$—COOR, —SR, —SAc).*

*wherein R is preferably H and Ac the acetyl group.

The invention, furthermore, concerns a process for the preparation of the dichloroisonitrilocarboxylic acid esters required for this purpose; i.e., isocyanide dihalogenides of aliphatic carboxylic acid esters.

Numerous methods for the preparation of these compounds are known, according to which, for example, salts of monosubstituted dithiocarbamic acids are converted into the mustard oils, then chlorinated, or their alkyl, cycloalkyl, or aryl derivatives are reacted by chlorination to isocyanide dichlorides (cf. Houben-Weyl, "Methoden der organischen Chemie" (Methods of Organic Chemistry) 4th ed., X: 869-873; Chem. Ber. 7: 1228, 1874; "Annalen der Chemie" (Annals of Chemistry) 663: 46 (1963); DAS No. 1,221,213).

Other methods for the preparation of these compounds reside in addition of halogen to isonitriles or in chlorination of monosubstituted formanilides (Angew. Chemie. (Applied Chemistry) 79 (1967) No. 15: 663-680; and Angew. Chemie 74 (1962) No. 21: 861-867).

These methods are of greatly varying suitability, depending on the starting material. According to the literature, aromatic formamides are predominantly employed if monosubstituted formamides serve as the starting material. In this process, the solvent is thionyl chloride, SOCl$_2$, and the compound which splits off chlorine is sulfuryl chloride, SO$_2$Cl$_2$. The yields are good only if the aromatic nucleus cannot be chlorinated as well on account of already present substituents, such as halogen, nitro, carboxy, and aryl residues. Substituents capable of reacting with thionyl chloride, for example, carboxy groups and carboxylic acid esters, yield the undesirable carboxylic acid chlorides (Angew. Chemie 74 (1962): 863; and Angew. Chemie 79 (1967): 667). Aliphatic and cycloaliphatic formamides react predominantly to form isocyanates so that, for example, N-cyclohexylformamide forms cyclohexylisocyanide dichloride only in yields of at most 60%.

Formamide derivatives of aliphatic carboxylic acid esters, thus, seemed to show little suitability for use in the preparation of isocyanide chlorides.

Consequently, the present invention has as its objective to provide a method that permits a technically simple production of dichloroisonitrilocarboxylic acid esters in high yields and purity.

Accordingly, this invention is also directed to a process for the production of substituted dichloroisonitrilocarboxylic acid esters of the formula:

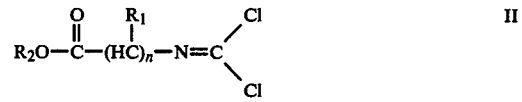

wherein
R$_1$ is an alkyl group containing 1 to 2 carbon atoms or hydrogen, n is an integer of from 1 through 4, and R$_2$ is an alkyl group containing 1 to 6 carbon atoms, characterized in that N-formylaminocarboxylic acid esters of the formula:

wherein R$_1$, R$_2$ and n have the same meaning as indicated above are reacted with chlorine or with a compound splitting off chlorine in thionyl chloride as the solvent.

The substituted dichloroisonitrilocarboxylic acid esters are derivatives of aliphatic monocarboxylic acid esters; i.e., of the acetic acid esters and the homologs thereof. The N-formylaminocarboxylic acid esters are of the type of substituted formamides.

The group —(CHR$_1$)$_n$— present in the product II and in the starting compound III can carry on one or more carbon atoms the substituent R$_1$; i.e., —CH$_3$ or —C$_2$H$_5$. Preferably when n is 1, the group —(CHR$_1$)$_n$ is —CH$_2$—; when n is 2, the group —(CHR$_1$)$_n$ is H$_3$C—CH$_2$— or —CH$_2$—CH$_2$—; and for certain cases, when n is 3, the group is then preferably —CH$_2$—CH$_2$—CH$_2$—.

In contrast to the cited literature, it is surprisingly possible to obtain from the formyl derivatives of the aliphatic aminocarboxylic acid esters the corresponding dichloroisonitriles without substantial proportions of isocyanates or acid chlorides in yields of more than 90% of theory and in high purity.

The starting compounds of Formula III are formed, for example, in a simple way by reacting aminocarboxylic acid ester hydrochlorides with formamide in toluene, in a quantitative yield.

The reaction to obtain compounds of Formula II is preferably conducted in SO$_2$Cl$_2$ as the compound splitting off chlorine. The molar ratio of the N-formylaminocarboxylic acid esters to chlorine or to the compound splitting off chlorine is 1:1 to 1:1.2. After the reaction is completed, the thionyl chloride, serving as the solvent, is removed, and the residue is distilled under reduced pressure. The temperatures can range between 20° and 85° C. The reaction is preferably performed under normal pressure. It is possible to add the compound splitting off chlorine; e.g., $SO_2Cl_2$, directly to the compound of Formula III without a solvent, but this results in comparatively lower yields in a range of 64 to 69% (Examples 4 and 5).

The reaction is preferably conducted at the boiling temperature of thionyl chloride, $SOCl_2$.

Very high yields of up to 95%, as well as high purities of the products of Formula II are obtained by a preferred mode of operation by adding the compound splitting off chlorine, especially $SO_2Cl_2$, and the starting compound of Formula III simultaneously into boiling thionyl chloride. In this procedure, about 10% of the $SO_2Cl_2$ is added initially to the $SOCl_2$.

The compounds of Formula II serve, for example, as the starting material for cyclization reactions with, for instance, alkaline azides, to obtain substituted tetrazole derivatives.

Another subject of this invention concerns the novel compounds represented by Formula II; i.e., dichloroisonitriloacetic acid ethyl ester, dichloroisonitrilo-α-methylacetic acid ethyl ester and dichloroisonitrilopropionic acid ethyl ester.

The processes of this invention and the compounds obtained thereby will be further understood from the following examples:

EXAMPLE A

Dichloroisonitriloacetic Acid Ethyl Ester (Starting Compound)

In a 2000 ml round flask, provided with four attachments and equipped with an agitator, reflux condenser, and two dropping funnels, a mixture of 1200 ml of $SOCl_2$ and 20 ml of $SO_2Cl_2$ is heated to boiling temperature; 232 ml (262 g=2 moles) of N-formylglycine ethyl ester and 150 ml of $SO_2Cl_2$ (in total 200 ml=233.4 g=2.47 moles) are added simultaneously, dropwise, to this solution. The reaction solution is then stirred for two hours at the above-indicated temperature. For working up purposes, the $SOCl_2$ is withdrawn under normal pressure, finally with the aid of a water-jet aspirator. The subsequent distillation at $bp_{12}=93°-96°$ C. yields 348 g=94.5% of theory of dichloroisonitriloacetic acid ethyl ester having a density of $n_D^{20}=1.4675$. Purity per gas chromatography is 96.8%.

The N-formylglycine ethyl ester employed can be obtained from glycine ethyl ester hydrochloride and 1.1 moles of formamide in toluene.

EXAMPLE 1

5-Chloro-1H-tetrazole-1-acetic Acid Ethyl Ester of Formula I

In a 1000 ml round flask equipped with an agitator a dropping funnel and reflux condenser, a mixture of 48.75 g (0.75 mole) of sodium azide in a solution of 180 ml of water and 360 ml of 1,2-dimethoxyethane is heated to a boiling temperature of about 80° C. Within one hour, 108 ml (1.38 g=0.75 mole) of dichloroisonitriloacetic acid ethyl ester of Formula II is added, dropwise, to this solution and, thereafter, the reaction solution is maintained at reflux temperature for one hour. In order to work up the reaction mixture, about 330 ml of dimethoxyethane is evaporated; the solution remaining in the flask is combined with 100 ml of water and cooled. The solution is seeded at 40° C. and further cooled to 15° C., thus obtaining a sediment of almost colorless crystals which are isolated by vacuum-filtering and dried under vacuum over potassium hydroxide.

Yield: 133.2 g of product (93.3% of theory), mp 56.5° C., purity more than 99% as per gas chromatography.

EXAMPLE 2

A flask equipped as described in Example 1 is charged with a mixture of 48.75 g (0.75 mole) of sodium azide in 180 ml of water and 360 ml of acetone; at 25° C., 108 ml (1.38 g=0.75 mole) of dichloroisonitriloacetic acid ethyl ester, diluted with 100 ml of acetone, is added, dropwise, to this solution and then the reaction solution is maintained for one hour at reflux temperature. The product was worked up as set forth in Example 1, thus obtaining 129 g of product (90.3% of theory), mp 56.5° C. which is the product of example 1.

EXAMPLE 3

5-Chloro-1H-tetrazole-1-propionic Acid Ethyl Ester

In a 1000 ml round flask, equipped with an agitator, a reflux condenser, a dropping funnel, and a thermometer, a mixture of 32.5 g (0.5 mole) of sodium azide in 120 ml of water and 240 ml of dimethoxyethane is heated to the boiling temperature—about 80° C.—and 103.1 g (content 96% strength=0.5 mole) of dichloroisonitrilopropionic acid ethyl ester is added, dropwise, within one hour to this solution. The reaction solution is then maintained for one hour at the reflux temperature. Thereafter, the dimethoxyethane is removed exhaustively up to $bp=9\pm°$ C. Upon cooling of the aqueous reaction solution to 10° C., an oily layer is separated and removed. The aqueous phase is extracted twice with, respectively, 100 ml of ether and then discarded. The oily phase and the ether extracts are combined, dried over sodium sulfate, and subsequently worked up by distillation after filtration of the drying agent. At $bp_{0.1}=63°-66°$ C., a fraction of 92.0 g=90% of theory is obtained.

EXAMPLE 4

Dichloroisonitriloacetic Acid Ethyl Ester

A 2000 ml round flask equipped with agitator, reflux condenser, and thermometer, is charged with a mixture, heated to 60° C., of 1200 ml of $SOCl_2$ and 100 ml (166.7 g=1.24 moles) of $SO_2Cl_2$; within 120 minutes, 116 ml (131 g=1 mole) of N-formylglycine ethyl ester is added, dropwise, to this reaction mixture. The latter is subsequently stirred for 60 minutes at 85° C. Thereafter, the unreacted $SO_2Cl_2$ and the solvent, $SOCl_2$, are removed, initially under normal pressure, toward the end with the aid of a water-jet aspirator and with a sump temperature of 40°-45° C.

Subsequent distillation of the thus-produced residue at $bp_{12}=92°-95°$ C. yields 127.3 g=69.2% of theory of the product, refractive index $n_D^{20}=1.4683$.

EXAMPLE 5

The apparatus described in Example 4 is charged, dropwise, at 20° C. with 116 ml (131 g=1 mole) of N-formylglycine ethyl ester in 1200 ml of $SOCl_2$ within 60 minutes; the temperature rises to 35° C. during this step. Thereafter, 200 ml (334 g=2.48 moles) of $SO_2Cl_2$ is added, dropwise, within 60 minutes, and the temperature is then increased to 75° C. and maintained at 75° C. for 60 minutes under agitation. A working up process as described in Example 4 yields, at $bp_{12}=90°-95°$ C., 118.5 g=64.4% of theory of the product of example 4; $n_D^{20}$=1.4685.

EXAMPLE 6

Dichloroisonitriloacetic Acid Ethyl Ester

In a 2000 ml round flask equipped with agitator, reflux condenser, and two dropping funnels, a mixture of 1200 ml of $SOCl_2$ and 20 ml of $SO_2Cl_2$ is heated to 75°–80° C.; simultaneously, 232 ml (262 g=2 moles) of N-formylglycine ethyl ether and 150 ml of $SO_2Cl_2$ (in total 233.4 g=2.47 moles of $SO_2Cl_2$) are added, dropwise, to this solution. After completion of the addition step, the reaction solution is stirred for two hours at the indicated temperature. For working up purposes, the $SOCl_2$ is removed first under normal pressure and toward the end of the distillation with the aid of a water-jet aspirator, thus recovering 990 ml=94.6% of theory of the $SOCl_2$ employed.

Subsequent distillation at $bp_{12}$=93°–96° C. yields 348 g of product=94.5% of theory as a colorless distillate of $n_D^{20}$=1.4675. Purity as per gas chromatography is 96.8%.

EXAMPLE 7

α-(Dichloroisonitrilo)propionic Acid Ethyl Ester

In a 1000 ml round flask equipped with agitator, reflux condenser, and two dropping funnels, a mixture of 400 ml of $SOCl_2$ and 5 ml of $SO_2Cl_2$ is heated to 65°–75° C.; simultaneously, 72 g of α-(N-formylamino)propionic acid ethyl ester ($bp_{20}$=141°–143° C.) and 50 ml of $SO_2Cl_2$ are added, dropwise, to this reaction solution. After a course of the reaction analogously to that of Example 3, subsequent distillation yields 83 g=88.7% of theory of a colorless distillate ($bp_{13}$=88°–90° C., $n_D^{20}$=1.4595).

EXAMPLE 8

β-(Dichloroisonitrilo)propionic Acid Ethyl Ester

The following reactants are employed under analogous conditions as in Example 4:
400 ml $SOCl_2$
10 ml $SO_2Cl_2$
and, thereafter,
100 g β-(N-formylamino)propionic acid ethyl ester ($bp_{18}$=149°–151° C.).

Yield: 119 g=89.6% of theory of a colorless distillate ($bp_{13}$=101°–103° C., $n_D^{20}$=1.4648).

EXAMPLE 9

5-Mercapto-1H-tetrazole-1-acetic acid (which is utilized as side chain of antibiotics)

In a 500 ml round flash equipped with agitator, relux condenser, thermometer and a dropping funnel a mixture of 100 g (0.52 mol) 5-Chloro-1H-tetrazole-1-acetic acid ethyl ester, 44 g (0,57 Mol) thiourea, 210 g water and 25 g of 38 wt.% aqueous hydrochloric acid was heated to reflux for 6 hours, while the ethanol formed during the reaction was distilled off. For working up purpose, the residue was extracted with methyl isobutyl ketone. After evaporation of the ketone 57.9 g=69% of the theory of a white crystalline solid (melting point 173° C.) of 5-Mercapto-1H-tetrazole-1-acetic acid was obtained (purity 99%).

This compound serves according to known methods as a side chain to form the cephalosporine CEFORANIDE.

What is claimed is:

1. A process for the production of a substituted dichloroisonitrilocarboxylic acid esters of the formula:

$$R_2O-\overset{O}{\underset{\|}{C}}-(HC)_n-\overset{R_1}{\underset{|}{N}}=C\overset{Cl}{\underset{Cl}{\diagup}} \quad (II)$$

wherein $R_1$ is an alkyl group containing 1 to 2 carbon atoms or hydrogen, n is an integer of from 1 through 4, and $R_2$ is an alkyl group containing 1 to 6 carbon atoms, which comprises reacting a N-formylaminocarboxylic acid ester of the formula:

$$R_2O-\overset{O}{\underset{\|}{C}}-(HC)_n-\overset{R_1}{\underset{|}{}}-HN-CHO \quad (III)$$

wherein $R_1$, $R_2$ and n have the meanings heretofore defined, with chlorine or with a compound splitting off chlorine in thionyl chloride as a solvent.

2. A process according to claim 1, wherein the reaction is conducted at boiling temperature of thionyl chloride, starting with the beginning of the reaction.

3. A process according to claim 1, wherein the compound splitting off chlorine is sulfuryl chloride.

4. A process according to claim 1, wherein the molar ratio of N-formylaminocarboxylic acid ester to chlorine and/or the compound splitting off chlorine is 1:1 to 1:1.2.

* * * * *